United States Patent
Dhanasingh et al.

(10) Patent No.: US 9,155,880 B2
(45) Date of Patent: *Oct. 13, 2015

(54) ELECTRODE WITH MOVABLE INSERTION STOPPER

(71) Applicant: MED-EL Elektromedizinische Geraete GmbH, Innsbruck (AT)

(72) Inventors: Anandhan Dhanasingh, Innsbruck (AT); Claude Jolly, Innsbruck (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 0 days.

This patent is subject to a terminal disclaimer.

(21) Appl. No.: 14/591,364

(22) Filed: Jan. 7, 2015

(65) Prior Publication Data

US 2015/0119791 A1    Apr. 30, 2015

Related U.S. Application Data

(63) Continuation-in-part of application No. 13/910,408, filed on Jun. 5, 2013, now Pat. No. 8,934,985.

(60) Provisional application No. 61/657,270, filed on Jun. 8, 2012.

(51) Int. Cl.
| | |
|---|---|
| *A61N 1/00* | (2006.01) |
| *A61N 1/05* | (2006.01) |
| *A61M 31/00* | (2006.01) |
| *A61B 17/34* | (2006.01) |
| *A61B 19/00* | (2006.01) |
| *A61N 1/36* | (2006.01) |

(52) U.S. Cl.
CPC ........... *A61N 1/0541* (2013.01); *A61M 31/002* (2013.01); *A61B 17/3468* (2013.01); *A61B 19/30* (2013.01); *A61B 2019/304* (2013.01); *A61N 1/36032* (2013.01)

(58) Field of Classification Search
USPC .................................................... 607/55, 137
See application file for complete search history.

(56) References Cited

U.S. PATENT DOCUMENTS

| | | |
|---|---|---|
| 8,934,985 B2 | 1/2015 | Dhanasingh et al. |
| 2006/0241723 A1 | 10/2006 | Dadd et al. |

(Continued)

OTHER PUBLICATIONS

International Searching Authority, International Search Report together with the Written Opinion for International Application No. PCT/US2013/044228 dated Jan. 31, 2014,16 pages.

(Continued)

*Primary Examiner* — Nicole F Lavert
(74) *Attorney, Agent, or Firm* — Sunstein Kann Murphy & Timbers LLP

(57) ABSTRACT

A cochlear implant electrode includes an electrode carrier having an electrode array with a groove disposed in a longitudinal direction along the electrode carrier, and a stopper positioned around the electrode carrier. The stopper has a protrusion on its inner surface that is configured to be positioned within the groove such that the stopper is movable with respect to the electrode carrier and a skirt disposed on a portion of its outer surface. Another configuration includes an electrode carrier having an electrode array with grooves disposed in a transverse direction along the electrode carrier, and a stopper positioned around the electrode carrier and configured to be positioned within each groove and movable with respect to the electrode carrier. The stopper has a skirt disposed on a portion of its outer surface.

21 Claims, 15 Drawing Sheets

(56) References Cited

U.S. PATENT DOCUMENTS

| | | |
|---|---|---|
| 2008/0119920 A1 | 5/2008 | Dadd et al. |
| 2009/0254163 A1 | 10/2009 | Gibson |
| 2011/0009877 A1 | 1/2011 | Thenuwara et al. |
| 2011/0245891 A1 | 10/2011 | Fritsch et al. |

OTHER PUBLICATIONS

International Searching Authority, Invitation to Pay Additional Fees with partial international search for International Application No. PCT/US2013/044228, 5 pages, Aug. 12, 2013.

26
Locking Grooves

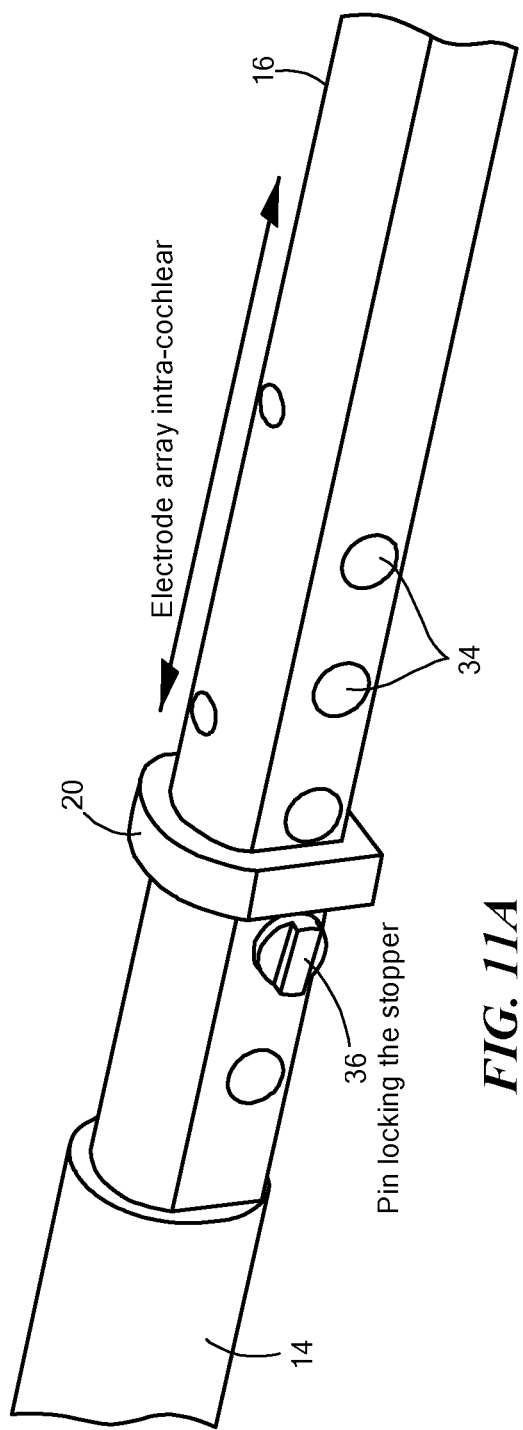
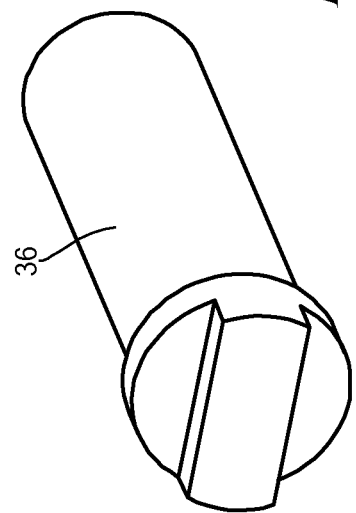
FIG. 11A
FIG. 11B

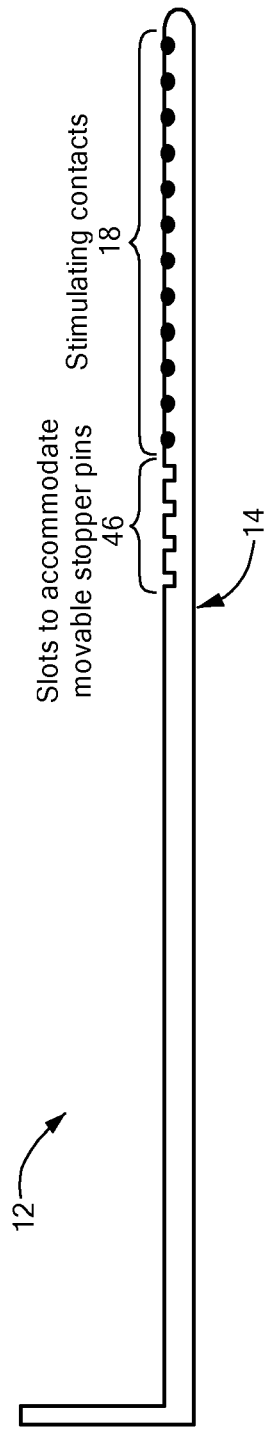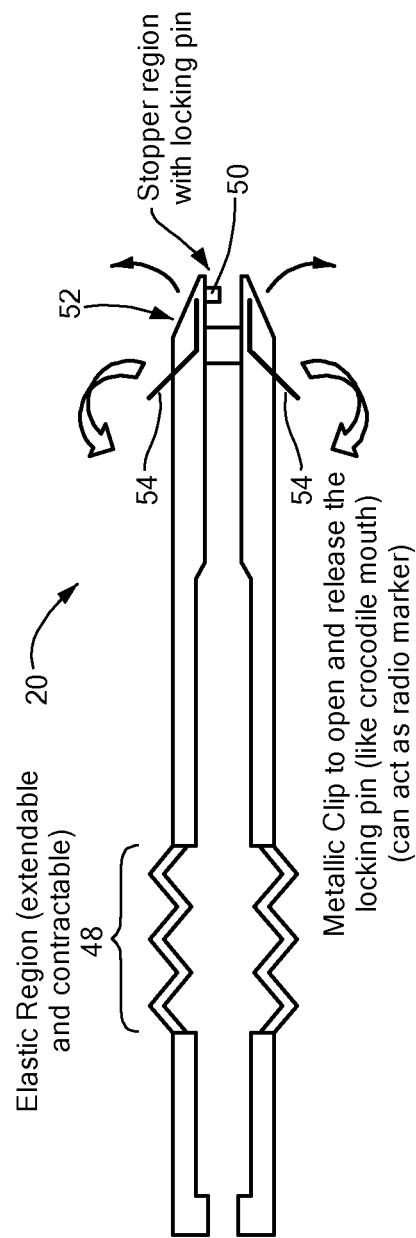
FIG. 16A
FIG. 16B

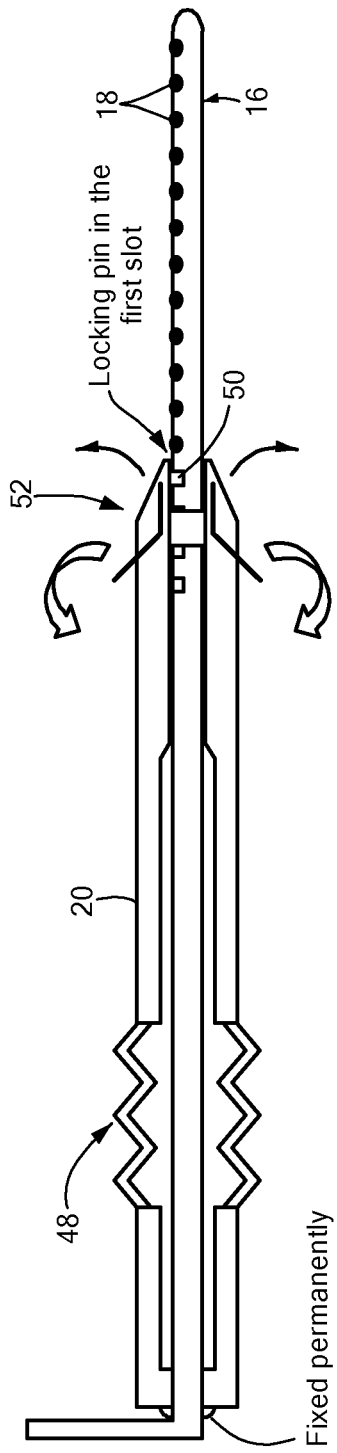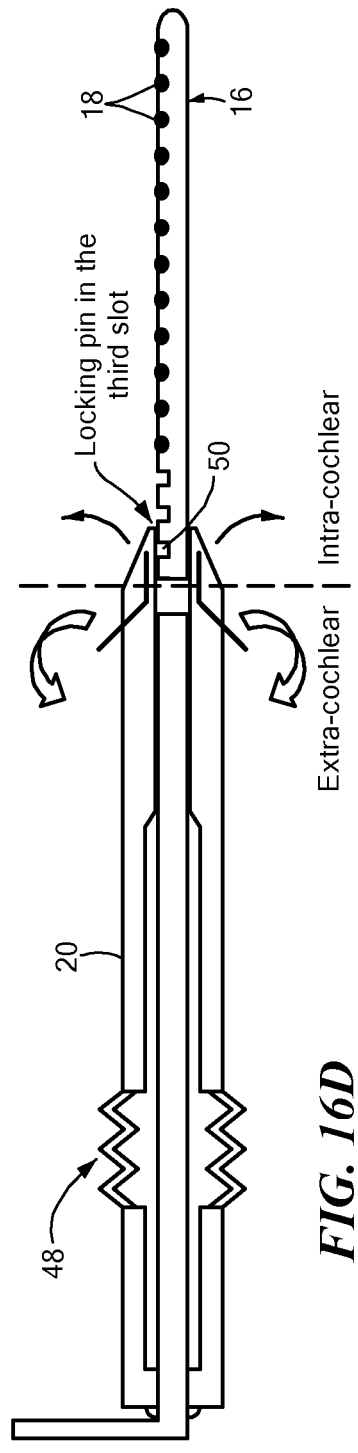

ELECTRODE WITH MOVABLE INSERTION STOPPER

CROSS-REFERENCE TO RELATED APPLICATIONS

This patent application is a continuation-in-part of U.S. patent application Ser. No. 13/910,408 filed Jun. 5, 2013, now U.S. Pat. No. 8,934,985, which claims priority to U.S. Provisional Patent Application No. 61/657,270 filed Jun. 8, 2012, the disclosures of which are incorporated by reference herein in their entirety.

TECHNICAL FIELD

The present invention generally relates to electrodes for medical implants and, more particularly, the invention relates to an electrode carrier with a movable insertion stopper that aids in the insertion process.

BACKGROUND ART

For many patients with severe to profound hearing impairment, there are several types of middle and inner ear implants that can restore a sense of partial or full hearing. For example, cochlear implants can restore some sense of hearing by direct electrical stimulation of the neural tissue of the cochlea. The cochlear implant typically includes an electrode carrier having an electrode lead and an electrode array, which is threaded into the cochlea. The electrode array usually includes multiple electrodes on its surface that electrically stimulate auditory nerve tissue with small currents delivered by the electrodes distributed along the electrode array. These electrodes are typically located toward the end of the electrode carrier and are in electrical communication with an electronics module that produces an electrical stimulation signal for the implanted electrodes to stimulate the cochlea.

One of the important steps in cochlear implant surgery is the insertion of the electrode array into the scala tympani of the cochlea. However, the cochlear duct length, i.e., the length measured from the round window entrance until the most apex of the cochlea (helicotrema), varies from patient to patient so no single electrode array length will be suitable for all patients. Literature shows that the cochlear duct length typically varies from about 25 mm to 35 mm. Thus, manufacturers of cochlear implants provide a wide range of electrode array lengths so as to cover the diversified cochlear duct length in patients. Some cochlear electrodes include a fixed insertion stopper to indicate the maximum insertion depth for the electrode array. The insertion stopper may also serve as a cap to close the round window opening, or cochleostomy site, where the electrode array is inserted into the cochlea.

In some cases, however, during the electrode insertion process, the electrode array is not inserted into the scala tympani beyond a certain insertion depth and stops well before the fixed insertion stopper reaches the cochleostomy due to a variety of situations, e.g., the electrode array length is too long for that particular cochlea, greater anatomical resistance inside the cochlea, insufficient experience with the surgeon, etc. In such situations, the closing of the round window opening or cochleostomy by the fixed insertion stopper is not possible and the exact electrode array entry point into the scala tympani cannot be determined or identified in radiographs that are taken after implantation.

SUMMARY OF EMBODIMENTS

In accordance with one embodiment of the invention, a cochlear implant electrode includes an electrode carrier having an electrode array with a groove disposed in a longitudinal direction along the electrode carrier, and a stopper positioned around the electrode carrier. The stopper has a protrusion on its inner surface that is configured to be positioned within the groove such that the stopper is movable with respect to the electrode carrier.

In accordance with another embodiment of the invention, a cochlear implant electrode includes an electrode carrier having an electrode array with grooves, each groove disposed in a transverse direction along the electrode carrier, and a stopper positioned around the electrode carrier. The stopper is configured to be positioned within each groove and movable with respect to the electrode carrier.

In accordance with another embodiment of the invention, a cochlear implant electrode includes an electrode carrier having an electrode array with notches disposed longitudinally along the electrode carrier and a stopper positioned over the electrode carrier. The stopper has a locking pin on an inner surface of its proximal end that is configured to be positioned within each notch and that is movable with respect to the electrode carrier. The stopper further including a flexible region configured to allow the stopper to expand or contract in length when the locking pin is moved with respect to the electrode carrier.

In accordance with another embodiment of the invention, a cochlear implant electrode includes an electrode carrier having an electrode array with a groove disposed in a longitudinal direction along the electrode carrier and a stopper positioned around the electrode carrier and having a protrusion on its inner surface that is configured to be positioned within the groove such that the stopper is movable with respect to the electrode carrier. The stopper includes a skirt disposed on a portion of its outer surface.

In accordance with another embodiment of the invention, a cochlear implant electrode includes an electrode carrier having an electrode array with grooves, each groove disposed in a transverse direction along the electrode carrier, and a stopper positioned around the electrode carrier. The stopper is configured to be positioned within each groove and movable with respect to the electrode carrier. The stopper includes a skirt disposed on a portion of its outer surface.

In some embodiments, the electrode array may include at least one locking groove disposed in a transverse direction such that the stopper is movable within the groove and within the locking groove. The stopper may further include a skirt around at least a portion of an outer surface of the stopper that is configured to cover at least a portion of a cochleostomy site. The skirt may be disposed on opposing sides of the stopper. The stopper may further include one or more break points configured to allow the stopper to break along the break points. The stopper may further include a band disposed inside the stopper that is made of a material that is detectable to radiography, such as a metal. The stopper may include an outer surface having two beveled surfaces with one beveled surface being smaller in diameter than the other beveled surface. The stopper may include an outer surface having the shape of two cone-shaped cylinders. The electrode may further include a clip secured to a position along the electrode array so that the stopper is prevented from moving beyond the position toward the distal end of the electrode carrier. The electrode array may further include at least one hole disposed in a transverse direction along the electrode carrier and the electrode may further include a pin configured to fit within the hole so that the stopper is prevented from moving beyond the pin toward the distal end of the electrode carrier. The inner surface of the stopper may be substantially similar in shape as an outer surface of the electrode carrier. For example, the inner surface of the stopper may be substantially round or circular in shape when fitting over an electrode carrier having a round or circular cross-section. Both the inner surface of the stopper and the outer surface of the electrode carrier may include a flat portion. In that case, the groove may be disposed on the flat portion of the electrode carrier and the protrusion may be disposed on the flat portion of the stopper. The stopper may include a drug that is released from the stopper in order to prevent bacterial infection or fibrous tissue formation at the round window opening or the cochleostomy. In some embodiments, the stopper is fixed to the electrode carrier at a distal end of the stopper. The stopper may further include a clip in its proximal end that is configured to open the stopper such that the locking pin disengages with the notch.

BRIEF DESCRIPTION OF THE DRAWINGS

The foregoing features of the invention will be more readily understood by reference to the following detailed description, taken with reference to the accompanying drawings, in which:

FIGS. 11A and 11B schematically show an electrode carrier having holes in the transverse direction and a pin, respectively, according to embodiments of the present invention;

FIGS. 16A-16D schematically show an electrode carrier and an extendable and contractible insertion stopper according to embodiments of the present invention.

DESCRIPTION OF ILLUSTRATIVE EMBODIMENTS

Various embodiments of the present invention provide a cochlear implant electrode that includes a movable insertion stopper positioned around the electrode carrier. The stopper may have a protrusion or locking pin on its inner surface that is positioned within, and is movable along, a longitudinal groove on the electrode carrier. Alternatively, the electrode carrier may have a series of grooves positioned in a transverse direction and a stopper that may be positioned within each groove and movable between the various grooves. Alternatively, the electrode carrier may have a series of notches or holes positioned along the carrier and a stopper that may have a locking pin on its inner surface that is positioned within each notch and movable between the various notches. The benefit of a movable insertion stopper is that the stopper may be moved to any point along the electrode carrier and fixed in a position close to the cochleostomy once the electrode array is inserted into the cochlea, regardless of the insertion depth of the electrode array. A movable insertion stopper that can be positioned close to the cochleostomy also provides a more accurate radio marker in post-implantation radiographs. A movable insertion stopper that can be positioned close to the cochleostomy and that covers and protects the electrode lead further reduces bacterial infection. Details of illustrative embodiments are discussed below.

Figure 1:
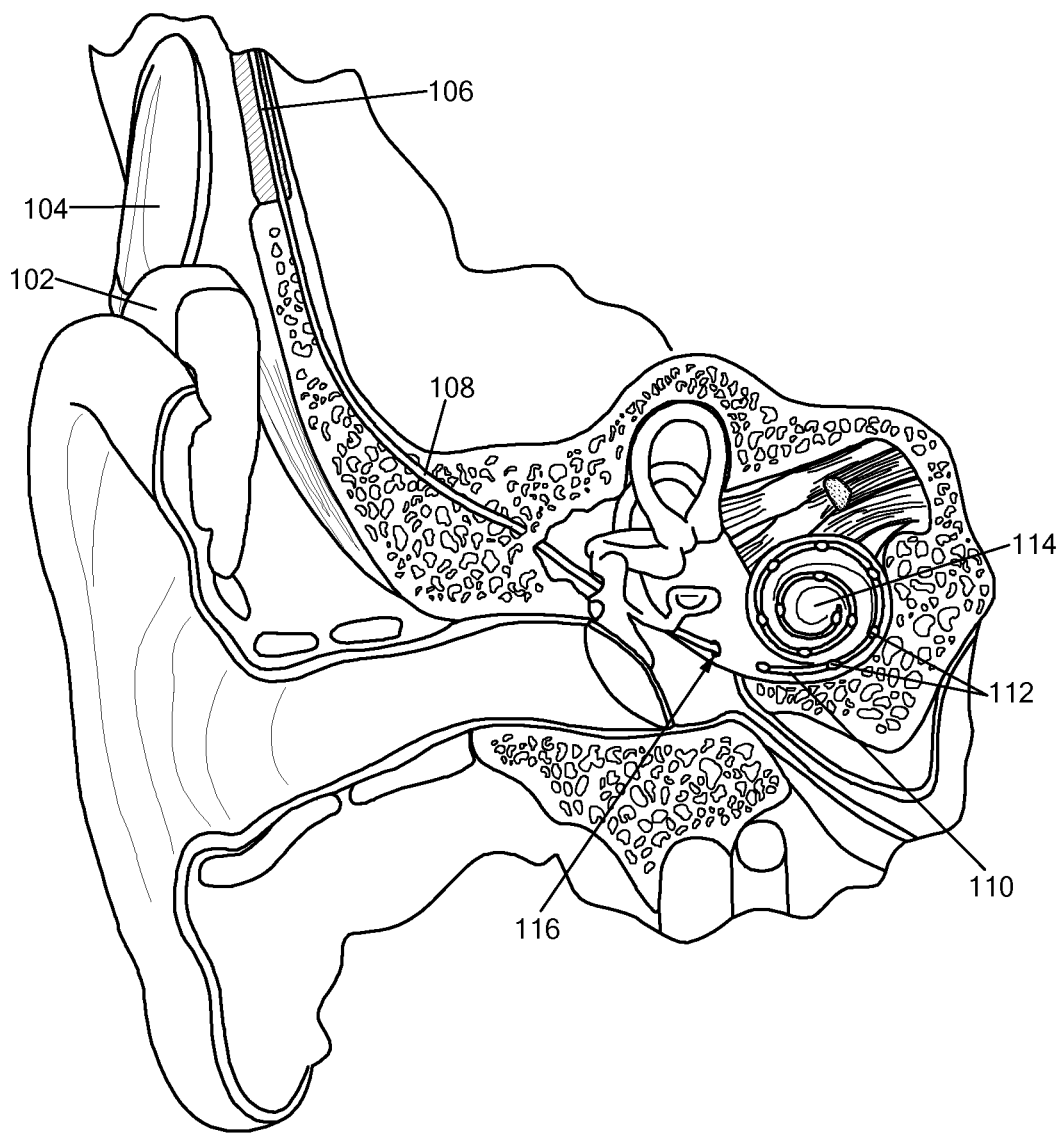
FIG. 1 schematically shows a typical human ear which includes a cochlear implant system.

FIG. 1 schematically shows the anatomy of a normal human ear and some components of a typical cochlear implant system. The cochlear implant system includes an external microphone (not shown) that provides an audio signal input to an external signal processor 102 where various signal processing schemes may be implemented. The processed signal is then converted into a stimulation pattern by an external transmitter/stimulator 104, and the stimulation pattern/signal is transmitted through connected wires (not shown) to an implanted electrode carrier 106. The electrode carrier 106 has an electrode lead 108 and an electrode array 110 that is inserted into the cochlea 114 through an opening in the round window or the cochleostomy site 116. Typically, the electrode array 110 has multiple electrodes 112 on its surface that provide selective stimulation to the cochlea 114.

Figure 2:
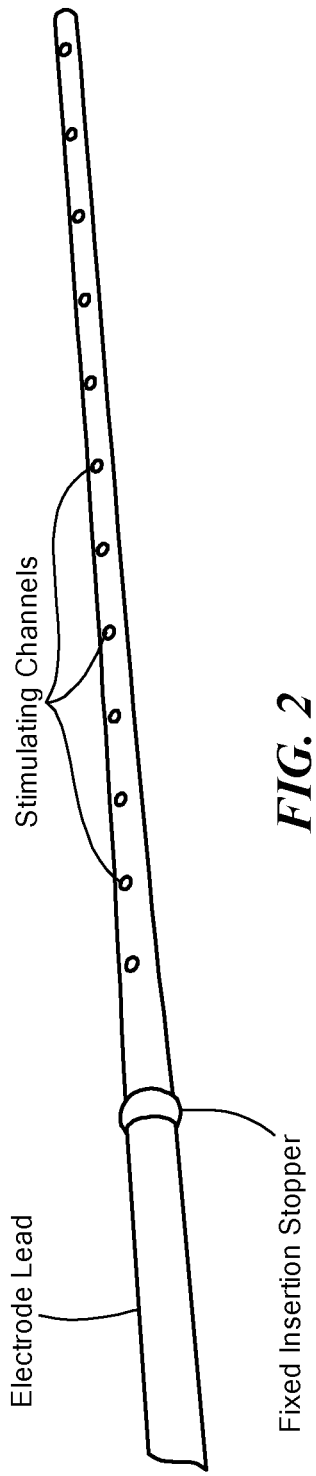
FIG. 2 schematically shows an electrode carrier with a fixed insertion stopper according to the prior art.

FIG. 2 schematically shows an electrode carrier with a fixed insertion stopper located between the electrode lead and the electrode array according to the prior art. As mentioned above, a fixed insertion stopper may not work as intended in situations where the electrode array is not fully inserted into the cochlea and stops well before the fixed insertion stopper reaches the cochleostomy.

Figure 3:
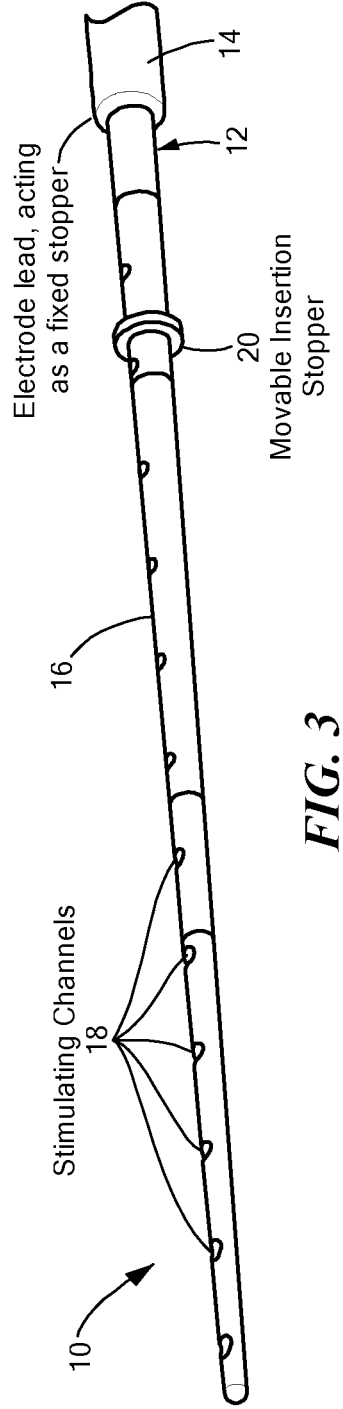
FIG. 3 schematically shows an electrode carrier with a movable insertion stopper according to embodiments of the present invention.
Figure 4:
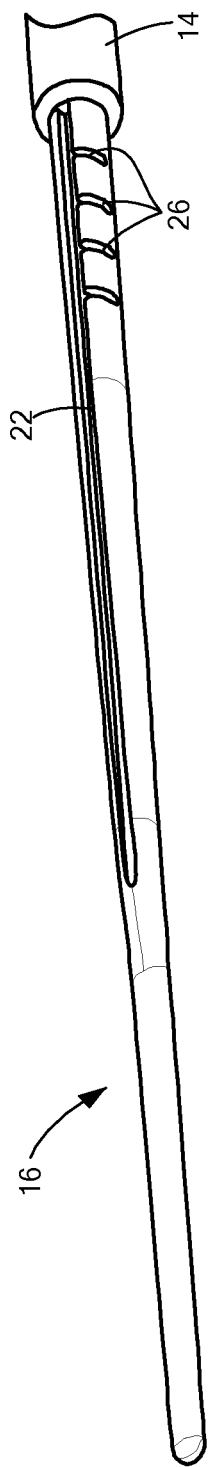
FIG. 4 schematically shows an electrode carrier with a longitudinal groove in the electrode array according to embodiments of the present invention.
Figure 5:
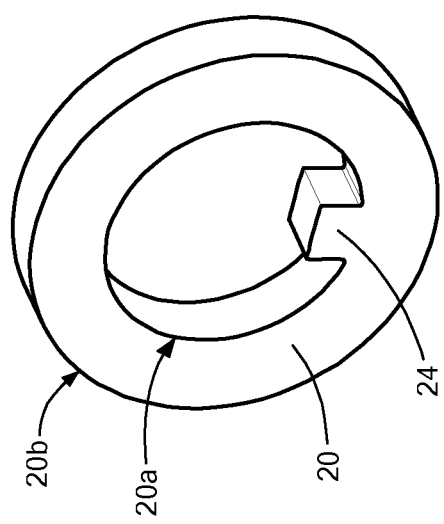
FIG. 5 schematically shows a movable insertion stopper with a protrusion or locking pin on its inner surface according to embodiments of the present invention.
Figure 6A:
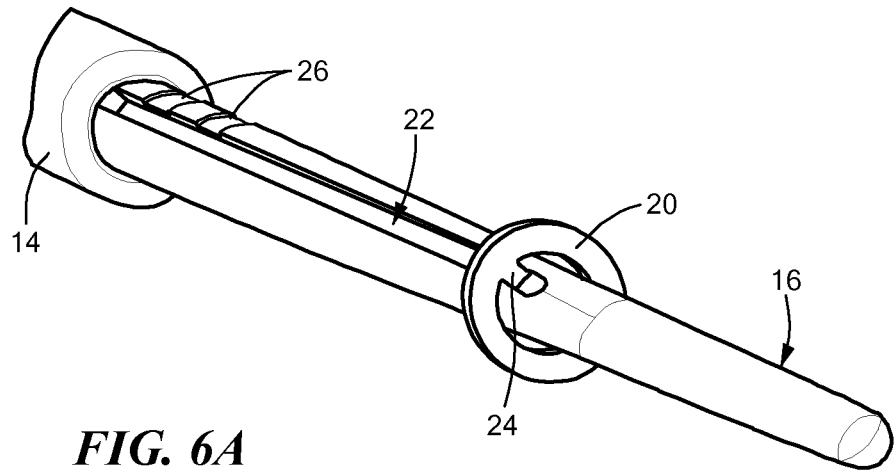
FIG. 6A schematically shows an electrode carrier with a movable insertion stopper according to embodiments of the present invention.
Figure 6B:
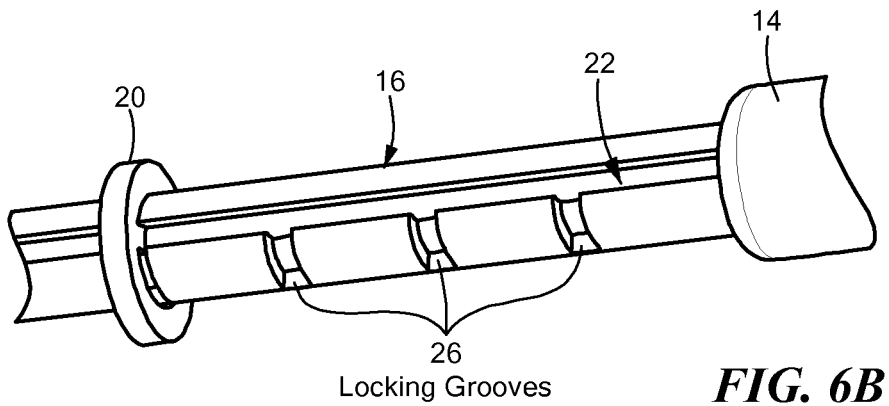
FIG. 6B schematically shows a portion of the electrode carrier with locking grooves according to embodiments of the present invention.
Figure 6C:
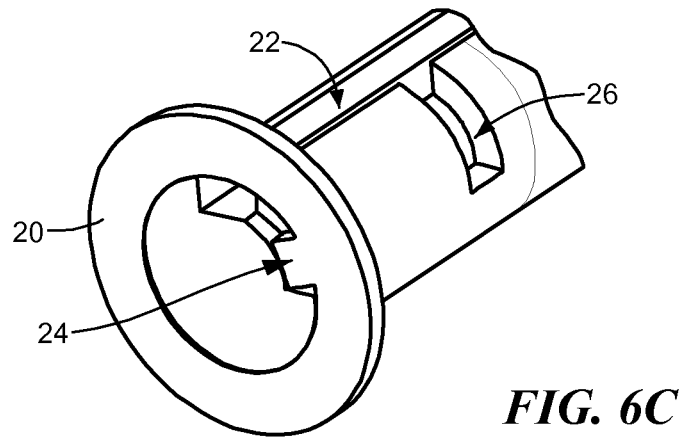
FIG. 6C schematically shows a cross-sectional view through one of the locking grooves of FIG. 6B.

FIG. 3 schematically shows an electrode 10 according to embodiments of the present invention. The electrode 10 includes an electrode carrier 12 having an electrode lead 14 at its distal end and an electrode array 16, with stimulating electrodes 18 distributed along the array, at its proximal end.

The electrode 10 also includes a movable insertion stopper 20 positioned around the electrode array 16 that is able to slide over the electrode array 16 without too much resistance. The insertion stopper 20 may be inserted over or completely removed from the electrode array 16. The insertion stopper 20 may be secured at any predefined position along the electrode array 16, as will be discussed in more detail below. The electrode lead 14 may serve as a fixed insertion stopper for the electrode, preventing the movable insertion stopper 20 from moving beyond the proximal end of the electrode lead 14 so that the electrode array 16 is not inserted too deeply into the cochlea of a patient. The insertion stopper 20 may be made of any biocompatible material such as biocompatible polymer, e.g., silicone which provides better flexibility or PTFE (Teflon) which provides better lubricity during moving and fixing of the insertion stopper along the electrode array 16.

Referring to FIGS. 4, 5 and 6A-6C, in a preferred embodiment, the electrode carrier 12 includes a groove 22 disposed in a longitudinal direction along the distal end of the electrode array 16. The insertion stopper 20 includes a protrusion or pin 24 on its inner surface 20a that is positioned within the groove 22 so that the insertion stopper 20 is movable with respect to the electrode carrier 12. The electrode carrier 12 may also include one or more locking grooves 26 disposed in a transverse direction on the electrode carrier 12. The insertion stopper 20 may be secured or locked at any predefined position on the electrode array 16 by rotating the insertion stopper 20 so that the protrusion 24 moves from the longitudinal groove 22 to the locking groove 26.

Figure 7A:
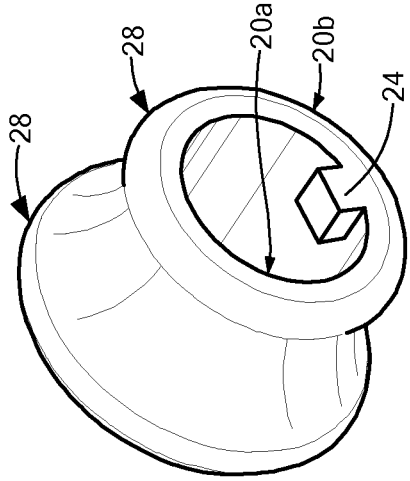
FIGS. 7A and 7B schematically show a side view and perspective view, respectively, of an insertion stopper with beveled surfaces according to embodiments of the present invention.
Figure 7B:
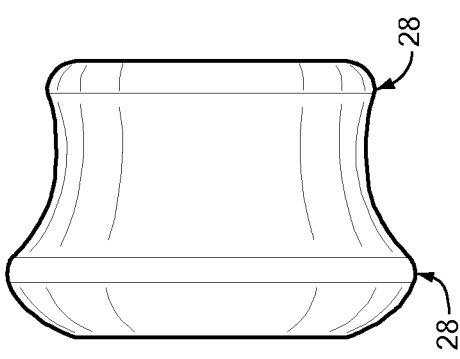
Figure 8:
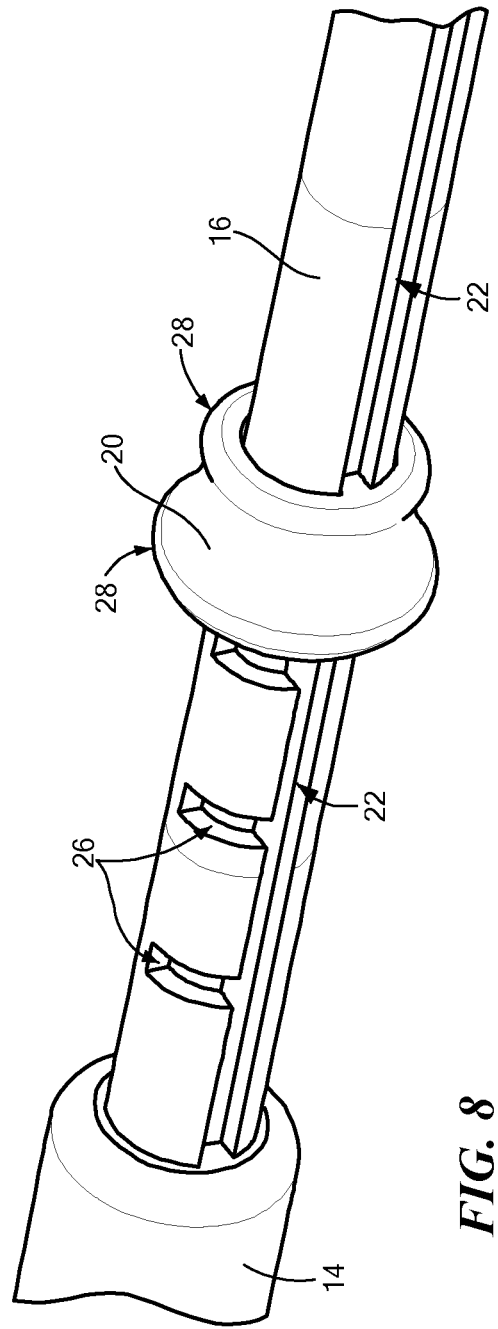
FIG. 8 schematically shows an electrode carrier with an insertion stopper with beveled surfaces according to embodiments of the present invention.
Figure 9B:
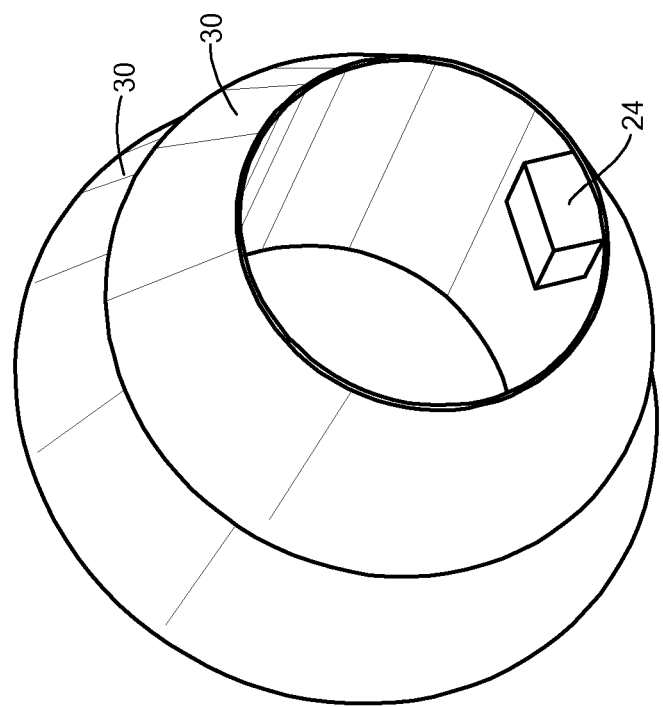
FIGS. 9A and 9B schematically show a side view and perspective view, respectively, of an insertion stopper in the shape of two cone-shaped cylinders according to embodiments of the present invention.
Figure 9A:
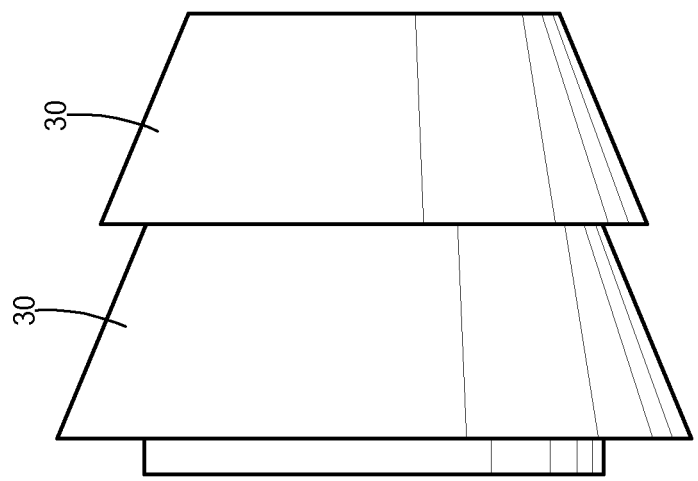

Although the insertion stopper 20 has been shown with an outer surface 20b that is round or circular in shape, other configurations may also be used. For example, the insertion stopper 20 may include an outer surface having one or more bulges or beveled surfaces 28, such as shown in FIGS. 7A, 7B and 8. If the configuration includes two beveled surfaces, then the diameter of the one beveled surface is preferably smaller than the diameter of the other surface, with the smaller beveled surface closer to the proximal end of the electrode array 16. As shown in FIGS. 9A and 9B, the insertion stopper 20 may have an outer surface shaped like one or more cone-shaped cylinders 30, with the smaller diameter portion of the cylinder closer to the proximal end of the electrode array 16. This type of configuration allows the smaller beveled surface or the smaller diameter cylinder to be at the front of the movable stopper 20 so that it can enter the round window opening or cochleostomy, which permits the electrode carrier 12 to be more readily affixed to the cochlea, so that any later movements of the electrode carrier 12 after implantation can be minimized or prevented.

Figure 10A:
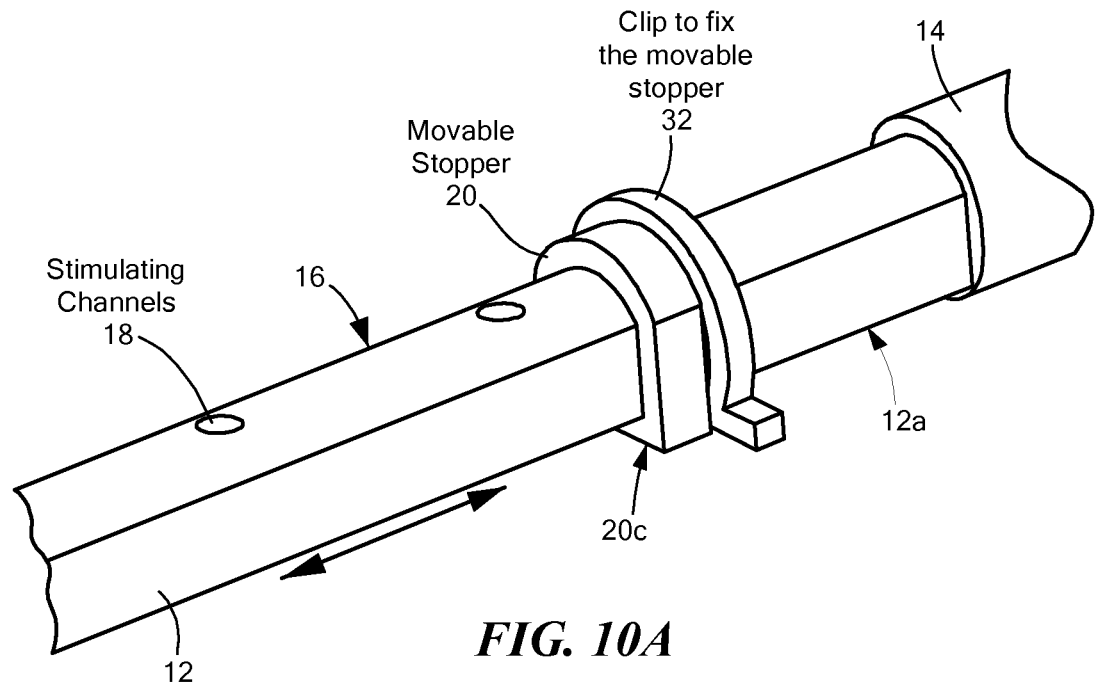
FIGS. 10A and 10B schematically show two perspective views of an electrode carrier and a stopper having a flat portion and a clip according to embodiments of the present invention.
Figure 10B:
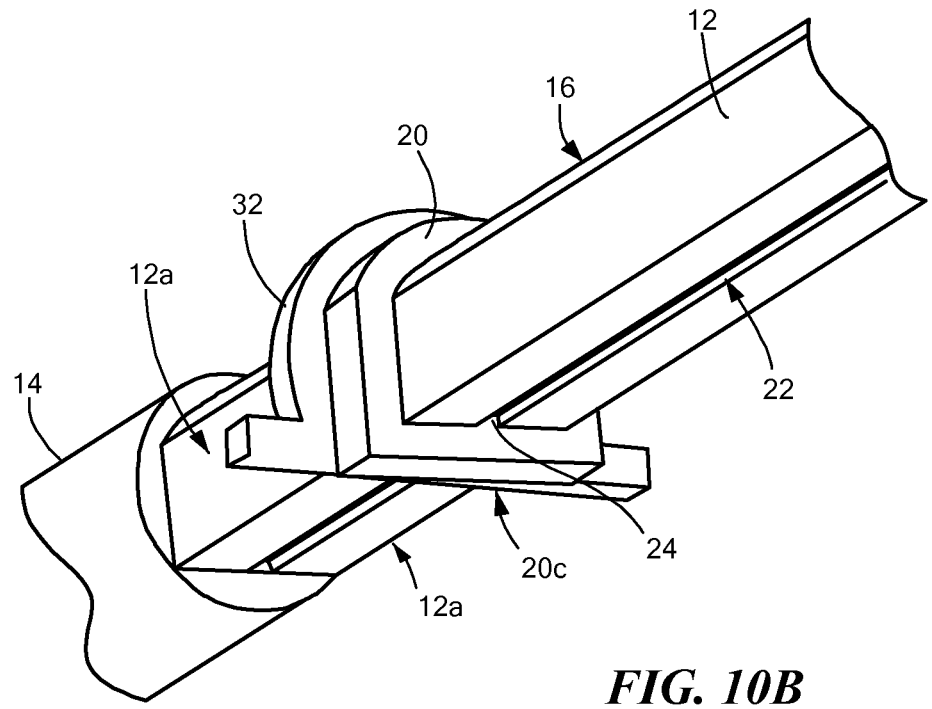

Although the outer surface of the electrode carrier 12 and the inner surface 20b of the insertion stopper 20 have been shown with a substantially round shape or circular cross-section, the electrode carrier 12 and stopper 20 may have other shapes. Preferably, the inner surface of the insertion stopper 20 is substantially similar in shape as the outer surface of the electrode carrier 12. For example, FIGS. 10A and 10B schematically show an electrode carrier 12 and an insertion stopper 20 having at least one flat portion. As shown in FIG. 10B, the longitudinal groove 22 may be disposed on a flat portion 12a of the electrode carrier 12 and the protrusion 24 may be positioned on a flat portion 20c of the insertion stopper 20. For an electrode carrier 12 which does not have a circular cross-section, the locking of the insertion stopper 20 may be accomplished in a number of ways rather than using the locking grooves 26. For example, a clip 32 may be used that is secured to a position along the electrode array 16, which prevents the insertion stopper 20 from moving beyond that position toward a distal end of the electrode carrier 12. Alternatively, the electrode carrier 12 may have one or more holes 34 located in the transverse direction along the electrode array 16 and a locking pin 36 that fits within the hole 34, as shown in FIGS. 11A and 11B. This type of configuration also prevents the insertion stopper 20 from moving beyond the pin 36 toward the electrode lead 14 in the distal end of the electrode carrier 12. The clip 32 and the locking pin 36 may be made of any biocompatible material such as biocompatible metal or any mechanically stable biocompatible polymer.

Figure 12A:
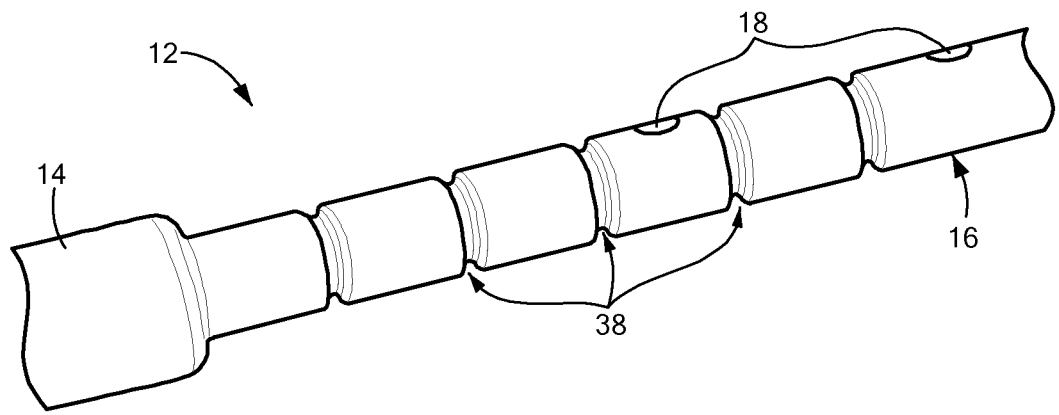
FIGS. 12A and 12B schematically show an electrode carrier having grooves in the transverse direction and an insertion stopper, respectively.
Figure 12B:
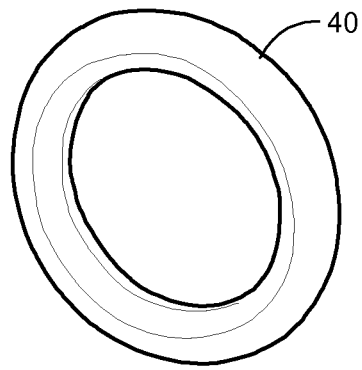
Figure 12C:
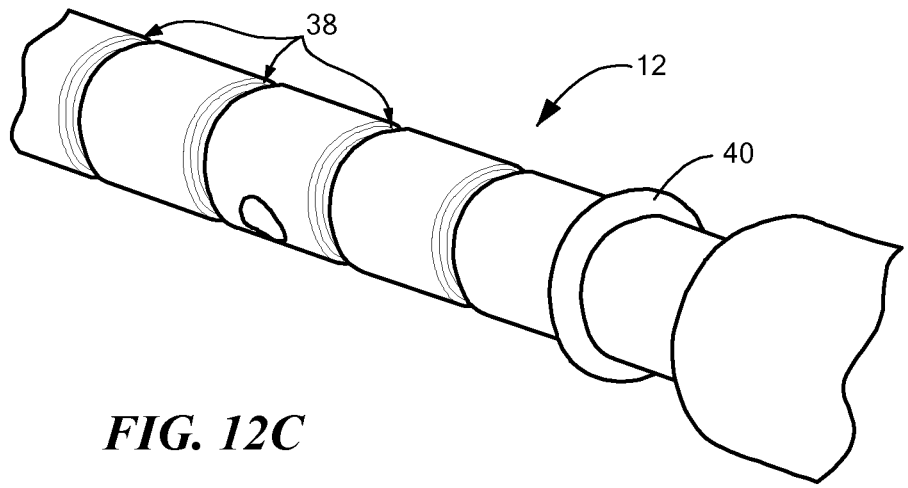
FIG. 12C shows the two components assembled together according to embodiments of the present invention.

Although an electrode carrier 12 with a longitudinal groove 22 is discussed above, other configurations may also be used that allow the insertion stopper 20 to be readily moved along the electrode array 16 and secured at different positions. For example, the electrode carrier 12 may include one or more grooves 38 disposed in the transverse direction along the electrode array 16 and an insertion stopper 40 that fits within the grooves 38, such as shown in FIGS. 12A through 12C. As shown in FIG. 12B, in this embodiment, the insertion stopper 40 does not have the protrusion 24 on its inner surface as previously shown and discussed in connection with insertion stopper 20. The transverse grooves 38 are located at predefined positions and the insertion stopper 40 may be moved parallel to the longitudinal axis of the electrode array 16 and positioned within any one of the grooves 38. The insertion stopper 40 and the electrode carrier 12 may be made of a biocompatible material, such as a silicone elastomer, which allows the insertion stopper 40 to be easily slid over the electrode carrier 12.

Figure 13A:
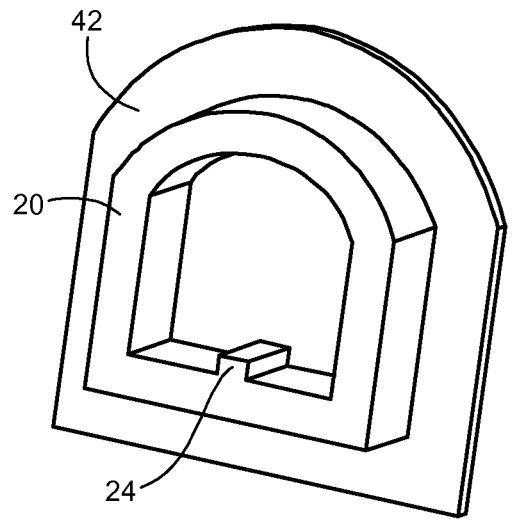
FIGS. 13A-13F schematically show different configurations of an insertion stopper having a skirt according to embodiments of the present invention.
Figure 13B:
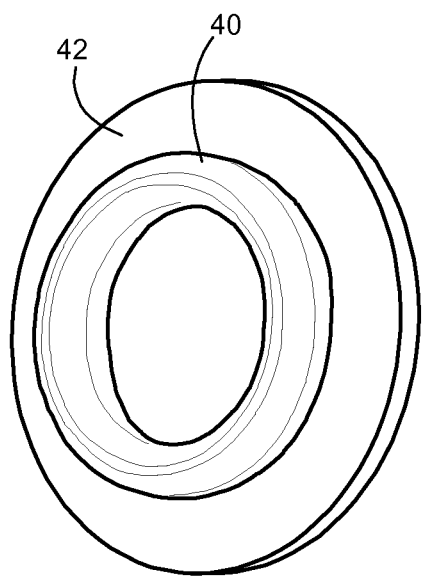
Figure 13C:
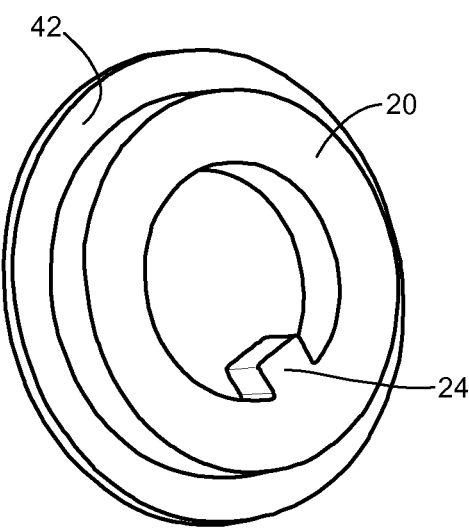
Figure 13D:
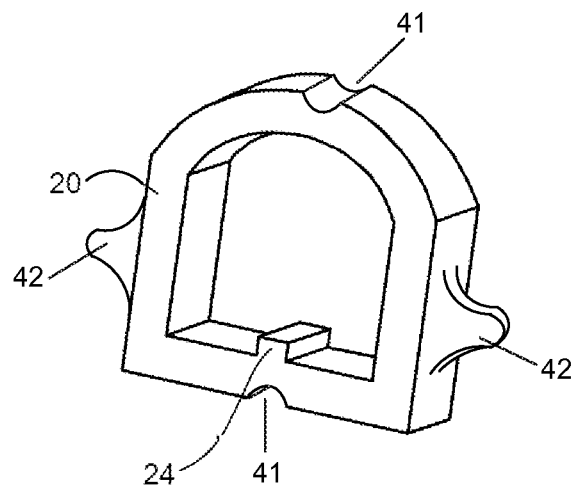
Figure 13E:
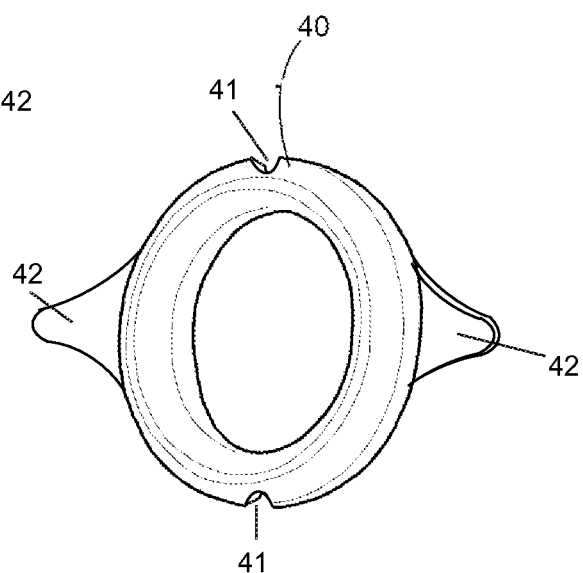
Figure 13F:
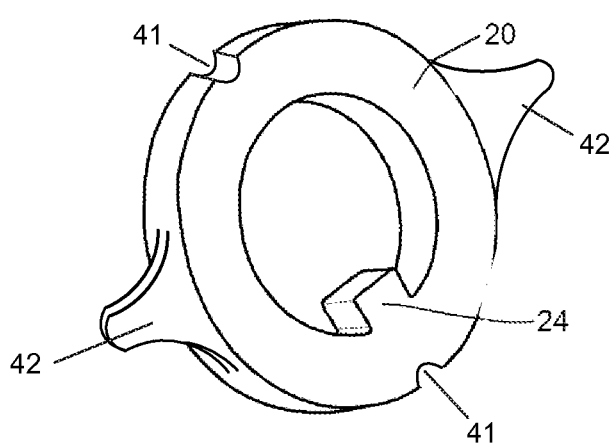

Other configurations of the stopper 20, 40 may also be used. For example, FIGS. 13A-13F show an insertion stopper 20, 40 having a skirt 42 around at least a portion of its circumference. The skirt 42 allows the electrode carrier 12 to be affixed to nearby tissue when the device is implanted and also may serve as a cap to help close the opening in the round window or cochleostomy. FIGS. 13A-13C show the skirt 42 completely surrounding the circumference of the insertion stopper 20, 40, and FIGS. 13D-13F show the skirt 42 in selected areas of the insertion stopper 20, 40. For example, as shown in FIGS. 13D-13F, the skirt 42 may be located on opposing sides so that the insertion stopper 20, 40 may be more easily grasped, e.g., with a surgical tool or with a surgeon's fingers. The skirt 42 may be thinner than the stopper 20, 40. In addition, the insertion stopper 20, 40, may include one or more predetermined break points 41, such as shown in FIGS. 13D-13F, formed in the stopper and configured to allow the insertion stopper 20, 40 to break along the break points 41. For example, if the skirt 42 is grasped and pulled apart or pulled back, the insertion stopper 20, 40 will break along the break points 41. The insertion stopper 20, 40 and its one or more break points 41 are configured such that the force normally applied while moving/sliding the insertion stopper 20, 40 in the grooves 22, 26 or into the grooves 38 does not break the insertion stopper 20, 40 apart. Therefore, the insertion stopper 20, 40 and break points 41 are configured so that the break force exceeds the moving force. The break points 41 may be on opposite sides of the insertion stopper 20, 40. For example, the skirt 42 may be located in two areas on opposing sides and the break points 41 may be located between the two areas, such as shown in FIGS. 13D-13F, so that the insertion stopper 20, 40 breaks into two parts. This configuration allows the surgical tool or fingers to securely hold the two areas of the skirt 42, preventing the parts from slipping out of the tool or fingers.

Figure 14A:
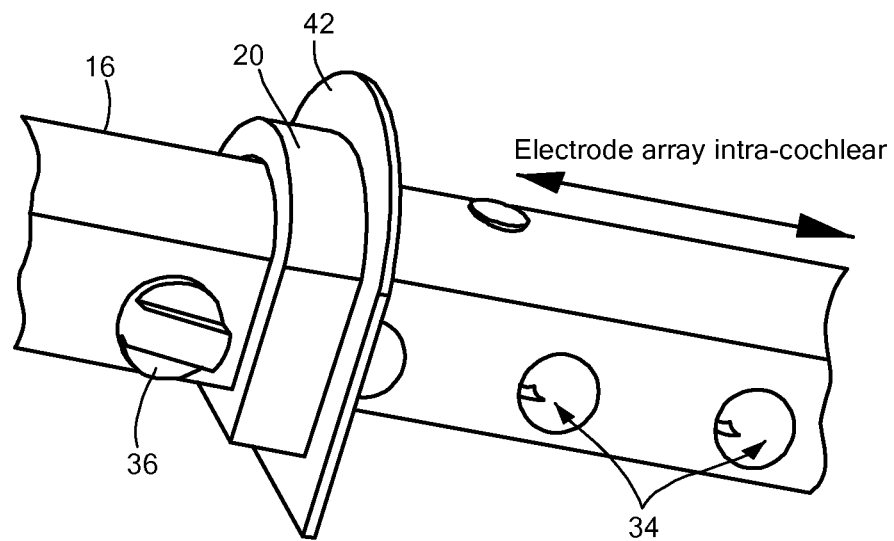
FIGS. 14A and 14B schematically show an electrode carrier and an insertion stopper having a skirt according to embodiments of the present invention.
Figure 14B:
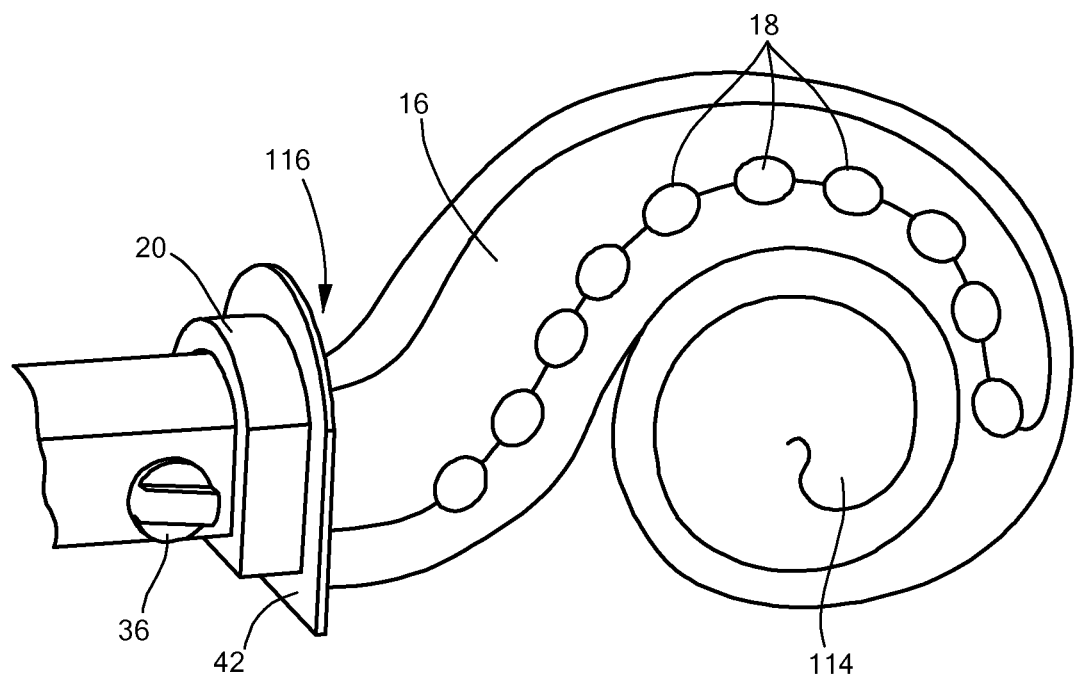
Figure 15A:
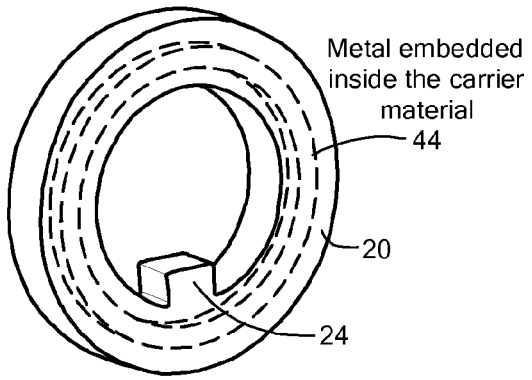
FIGS. 15A-15E schematically show different configurations of an insertion stopper having a band according to embodiments of the present invention.
Figure 15B:
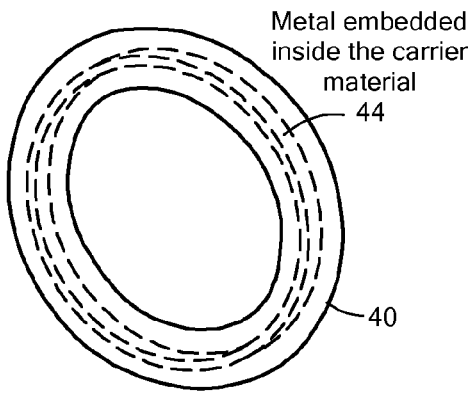
Figure 15C:
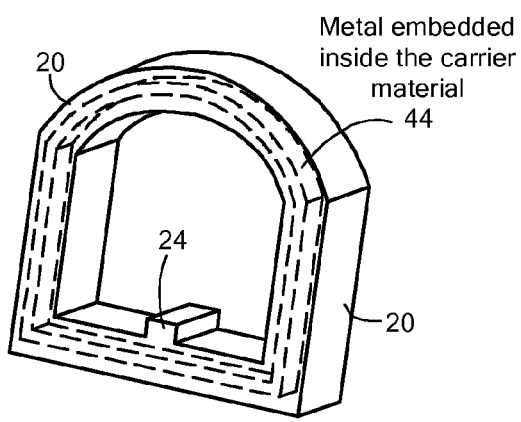
Figure 15D:
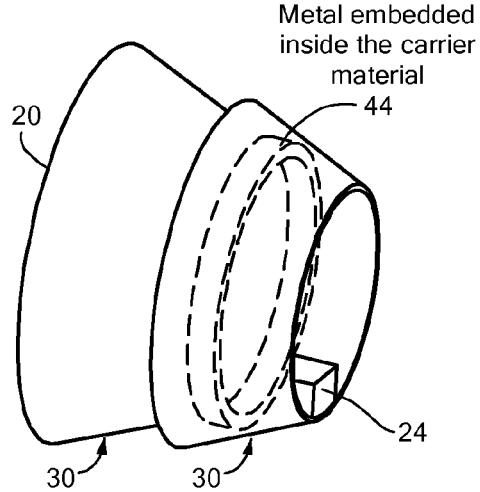
Figure 15E:
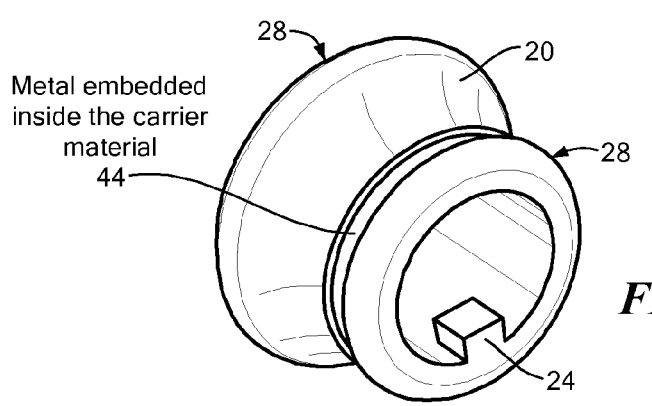

FIG. 14A shows an electrode carrier 12 assembled with an insertion stopper 20 having a skirt 42 and FIG. 14B schematically shows the electrode array 16 implanted within the cochlear 114 with the insertion stopper 20 provided near the cochleostomy 116. Instead of, or in addition to, the skirt 42, the insertion stopper 20, 40 may be secured to the cochlea or the nearby tissue by any biocompatible tissue glue, for example, fibrin glue, biocompatible quick polymer glue, etc. The skirt 42 may be made of the same material as that of the insertion stopper 20, 40. The insertion stopper 20, 40 may be embedded or loaded with any drug molecules so that the drug is released from the insertion stopper 20, 40 in order to prevent bacterial infection or fibrous tissue formation at the round window opening or the cochleostomy.

As shown in FIGS. 15A-15E, the insertion stopper 20, 40 may have a band 44 that is embedded within the insertion stopper 20, 40. The band 44 may be made of any biocompatible material that is detectable in radiographs. When the insertion stopper 20, 40 is positioned close to the cochleostomy after the electrode array 16 is implanted in the cochlea, the band 44 serves as a radio marker to more accurately determine the location of the electrode carrier 12 and cochleostomy in post-implantation radiographs.

FIGS. 16A-16D show an electrode carrier 12 and movable insertion stopper 20 configuration that covers and protects the electrode lead which reduces bacterial infection. In this embodiment, the electrode carrier 12 includes notches 46 and the movable insertion stopper 20 has a flexible region 48 that is configured to extend or contract depending on the relative position of the stopper 20 in relation to the carrier 12. The movable insertion stopper 20 is configured to fit over the electrode lead 14 and includes a locking pin 50 on its inner surface that is configured to engage with and be positioned within the notches 46 on the electrode carrier 12. The insertion stopper 20 may include a conical stopper region 52 at its proximal end and may be securely fixed to the electrode carrier 12 at the distal end of the stopper 20, e.g., using silicone or other suitable fixing means. As shown in FIGS. 16C and 16D, the flexible region 48 allows the insertion stopper 20 to expand or contract in length in order to accommodate the locking pin 50 in the various notch 46 positions. The insertion stopper 20 may include a clip 54, e.g., a metallic clip, in its proximal end that is configured to open the stopper region 52 such that the locking pin 50 disengages with the notch 46. The clip 54 may be detectable in radiographs and serve as a radio marker, similar to the band 44 previously described. The clip 54 may be fixed to the nearby bone, tissue, or round window niche to prevent electrode spring back. In addition, the insertion stopper 20 in this embodiment may further include a skirt 42, such as shown and described with regard to FIGS. 13A- 13C.

Although the above discussion discloses various exemplary embodiments of the invention, it should be apparent that those skilled in the art can make various modifications that will achieve some of the advantages of these embodiments without departing from the true scope of the invention.

What is claimed is:

1. A cochlear implant electrode comprising:
    an electrode carrier having an electrode array with a groove disposed in a longitudinal direction along the electrode carrier; and
    a stopper positioned around the electrode carrier, the stopper having a protrusion on an inner surface of the stopper, the protrusion configured to be positioned within the groove so that the stopper is movable with respect to the electrode carrier, the stopper having a skirt disposed on a portion of its outer surface.

2. The electrode of claim 1, wherein the electrode array further includes at least one locking groove disposed in a transverse direction such that the stopper is movable within the groove and within the locking groove.

3. The electrode of claim 1, wherein the skirt is disposed on opposing sides of the stopper.

4. The electrode of claim 1, wherein the stopper includes an outer surface having two beveled surfaces, wherein one beveled surface has a smaller diameter than the other beveled surface.

5. The electrode of claim 1, wherein the stopper includes an outer surface having a shape of at least one cone-shaped cylinder.

6. The electrode of claim 1, wherein the stopper further includes a band disposed inside the stopper, the band made of a material that is detectable in radiographs.

7. The electrode of claim 1, wherein the stopper further includes one or more break points configured to allow the stopper to break along the break points.

8. The electrode of claim 1, further comprising a clip secured to a position along the electrode array so that the stopper is prevented from moving beyond the position toward a distal end of the electrode carrier.

9. The electrode of claim 1, wherein the electrode array further includes at least one hole disposed in a transverse direction along the electrode carrier, the electrode further comprising a pin configured to fit within the hole so that the stopper is prevented from moving beyond the pin toward the distal end of the electrode carrier.

10. The electrode of claim 1, wherein the inner surface of the stopper is substantially round in shape.

11. The electrode of claim 1, wherein the inner surface of the stopper is substantially similar in shape as an outer surface of the electrode carrier.

12. The electrode of claim 11, wherein the inner surface of the stopper includes a flat portion and the outer surface of the electrode carrier includes a flat portion.

13. The electrode of claim 12, wherein the groove is disposed on the flat portion of the electrode carrier and the protrusion is disposed on the flat portion of the stopper.

14. The electrode of claim 1, wherein the stopper includes a drug that is released from the stopper in order to prevent bacterial infection or fibrous tissue formation.

15. A cochlear implant electrode comprising:
    an electrode carrier having an electrode array with grooves, each groove disposed in a transverse direction along the electrode carrier; and
    a stopper positioned around the electrode carrier, the stopper configured to be positioned within each groove and movable with respect to the electrode carrier, the stopper having a skirt disposed on a portion of its outer surface.

16. The electrode of claim 15, wherein the skirt is disposed on opposing sides of the stopper.

17. The electrode of claim 15, wherein the stopper further includes a band disposed inside the stopper, the band made of a material that is detectable in radiographs.

18. The electrode of claim 15, wherein the stopper includes an outer surface having two beveled surfaces, wherein one beveled surface has a smaller diameter than the other beveled surface.

19. The electrode of claim 15, wherein the stopper includes an outer surface having a shape of at least one cone-shaped cylinder.

20. The electrode of claim 15, wherein the stopper includes a drug that is released from the stopper in order to prevent bacterial infection or fibrous tissue formation.

21. The electrode of claim 15, wherein the stopper further includes one or more break points configured to allow the stopper to break along the break points.

\* \* \* \* \*